United States Patent

Römisch et al.

Patent Number: 6,117,647
Date of Patent: Sep. 12, 2000

[54] PROCESS FOR QUANTIFYING GLYCOSAMINOGLYCANS IN ANTITHROMBIN III-CONTAINING SOLUTIONS

[75] Inventors: Jürgen Römisch, Marburg; Harald Stauss, Dautphetal, both of Germany

[73] Assignee: Aventis Behring GmbH, Marburg, Germany

[21] Appl. No.: 08/910,121

[22] Filed: Aug. 13, 1997

[30] Foreign Application Priority Data

Aug. 17, 1996 [DE] Germany .......................... 196 33 214

[51] Int. Cl.[7] .......................... G01N 33/53; G01N 1/18; C12Q 1/56; C12P 21/06
[52] U.S. Cl. .......................... 435/13; 435/7.92; 435/13; 435/69.6; 435/962; 436/69; 436/177; 436/178; 436/825; 530/380; 530/381; 530/382; 530/383; 530/384
[58] Field of Search .......................... 435/7.92, 13, 69.6, 435/962; 436/69, 177, 178, 825; 530/380, 381, 382, 383, 384

[56] References Cited

U.S. PATENT DOCUMENTS 5,304,638 4/1994 Marshall et al. .......................... 530/383

5,320,945 6/1994 Dessauer et al. .......................... 435/13

FOREIGN PATENT DOCUMENTS

0217768 A2 4/1987 European Pat. Off. .
0657547 A1 6/1995 European Pat. Off. .

OTHER PUBLICATIONS

Gressner et al. J. Clin. Chem. & Clin. Biochem. vol. 21; pp. 407–416, 1983.

*Primary Examiner*—James C. Housel
*Assistant Examiner*—Gailene R. Gabel
*Attorney, Agent, or Firm*—Finnegan, Henderson, Farabow, Garrett & Dunner, L.L.P.

[57] ABSTRACT

A process for determining glycosaminoglycans in antithrombin III (ATIII)-containing solutions by increasing the ionic strength of the AT III-containing solution until the interaction between AT III and glycosaminoglycans is prevented, removing the AT III which has been released from the glycosaminoglycans from the solution, and desalting and determining the glycosaminoglycan which has remained in the solution.

5 Claims, No Drawings

PROCESS FOR QUANTIFYING GLYCOSAMINOGLYCANS IN ANTITHROMBIN III-CONTAINING SOLUTIONS

A process is described which makes it possible to determine glycosaminoglycans (GAG), e.g. heparin, quantitatively in antithrombin III-containing solutions and solutions which contain other GAG-binding proteins.

Antithrombin III is a protein which belongs to the serine protease inhibitor family. By forming complexes with proteases, such as thrombin, coagulation factor Xa, etc., AT III inhibits the proteolytic activities of these enzymes. Through the range of inhibited proteases, AT III contributes to the regulation of hemostasis. In association with a blood vessel lesion, for example, this inhibitor permits cessation of bleeding by the progressive nature of the inhibition of coagulation factors: complete inhibition of the activated coagulation proteases is only concluded when wound closure (fibrin, platelets) has taken place.

On the other hand, AT III is bound, for example, to the blood vessel endothelium by way of glycosaminoglycans (GAGs) and in this way prevents uncontrolled fibrin formation/thrombus formation at the vessel wall. In this context, GAGs are not only used as receptors but also accelerate the reaction of AT III with proteases. As a result of this noncovalent interaction of AT III and heparin or heparan sulfate, for example, a conformational change takes place in the inhibitor molecule which enables the rate of complex formation with the protease to be increased. For simplicity, this effect is termed "activation".

Therapeutic use is made of this acceleratory effect by, for example, administering heparin, which is regarded as being a GAG, for thrombosis prophylaxis. When coagulation cascades, such as frequently occur, for example, during/after operations, are activated, some of the proteases which are generated are inhibited efficiently and rapidly by AT III/heparin and the risk of thrombus formation is thereby reduced.

Since, by contrast, hemorrhages can occur when an overdose of heparin is given, the heparin plasma level of the patient has to be monitored and measures such as neutralization with protamine resorted to if necessary.

Methods for assessing the heparin concentration in the plasma have been used for a long time. These methods are based, for example, on using dextran sulfate (DXS) to displace heparin, which is partially bound to AT III or other GAG-binding proteins, from the bond. The subsequent detection systems are not significantly affected, in contrast to heparin, by DXS at these concentrations. These detection systems are in turn based on reacting heparin, which has been liberated by DXS, with a defined quantity of AT III, which is added to the solution. The quantity of added protease, for example Xa, which is not inhibited by AT III/heparin is determined photometrically using a chromogenic substrate. Coagulometric methods are also employed.

The quantity of heparin in a sample is calculated from a standard curve which is plotted using increasing quantities of heparin. Appropriate tests having a sensitivity of merely 0.5 or 0.1 IU/ml are available, with these tests corresponding to therapeutically meaningful and important heparin levels.

By contrast, antithrombin III concentrates are administered therapeutically, for example to patients who are suffering from a congenital or acquired AT III deficiency. Since immobilized heparin is used to purify a number of these preparations from plasma fractions, for example, it is of interest to quantify heparin in these concentrates. For testing, these concentrates have to be employed in as concentrated a form as possible in order to be at all able to detect or quantify the quantities of heparin, which are usually only present in traces. Since the AT III concentrations in this context are frequently of the order of 20 IU/ml or more (corresponding to 3 mg of AT III/ml or more), established test systems are perturbed simply by the progressively inhibitory potential of the AT III, thereby leading to false results. In accordance with this, the concentrate then has to be diluted until this progressive activity can be disregarded. This frequently means, in turn, that the heparin traces can no longer be detected using the normal tests. For comparative purposes, a typical commercial assay contains 1 IU of AT III/ml which is used to quantify the heparin concentration in a sample.

The object of this invention is therefore to make available a process for quantifying heparin in AT III-containing solutions, which process is independent of the AT III concentration of this solution.

The object is achieved as follows:

1. The ionic strength of the AT III-containing solution is increased until the interaction between AT III and heparin is prevented or heparin is quantitatively released from the noncovalent bond. Ionic strengths of between 15 and 250 mS, preferably of between 25 and 150 mS, are used. These ionic strengths are achieved, for example, by adding appropriate quantities of salts, for example NaCl, or appropriate volumes of highly concentrated stock solutions.

As compared with conventional processes, this process offers the advantage that there is no need to add DXS. This is particularly advantageous in the case of very high AT III concentrations since, in these cases, extreme quantities of DXS would have to be added, with these quantities then interfering with the subsequent detection system.

2. AT III is removed from this solution, for example using matrix-coupled antibodies against AT III. In a preferred procedure, AT III is precipitated out of the solution and is separated off by, for example, centrifuging or filtering. At the same time, heparin remains quantitatively in the supernatant. Precipitations can be carried out using suitable quantities of ammonium sulfate, for example. An acid, particularly preferably trichloroacetic acid (0.05 M—saturated, preferably 0.5–2 M), is preferably used for denaturing and then separating off.

3. The excess of acid or salt is lowered, for example by dialysis, with it being necessary to prevent the sample from being strongly diluted in order to ensure that heparin traces can be detected. Since they save time and are easy to standardize, preference is given to using so-called desalting and salt-changing columns, which are known to the skilled person as gel filtration columns. The diluting effect on the sample is small.

4. The resulting heparin-containing solution is quantified in a suitable test system. Suitable test systems are understood as meaning, for example, coagulometric or chromogenic/fluorigenic assays which are generally based on the cofactor activity of the GAGs (see above). Immunochemical tests, such as ELISA, using antibodies which are directed against the GAGs to be determined, may also be used. Other suitable methods are chromatographic techniques, such as HPLC, or quantitative electrophoreses.

The process which is described is not restricted to heparin but also includes other GAGs, such as heparan sulfate, dermatan sulfate, chondroitin sulfate, etc.

On the other hand, it can also be used to determine GAGs which are bound to proteins other than AT III. Examples of these proteins are heparin cofactor II, tissue factor pathway inhibitor, protein C inhibitor or platelet factor 4.

The process is clarified by the following example:

EXAMPLE

Different quantities of heparin were added to an AT III concentrate. Following a one-hour incubation, the solution was treated as follows:

1. Bound heparin was released from its complex with AT III by adding NaCl;
2. AT III was removed by adding trichloroacetic acid and centrifuging;
3. The supernatant was desalted and the TCA removed by means of NAP-5 gel filtration;
4. The eluate was tested in a chromogenic assay; the heparin concentration was quantified using a standard curve.

Antithrombin III concentrate (Kybernin®P, Centeon Pharma GmbH) was dissolved to give a concentration of 50 IU/ml, and 0, 20, 50 and 80 mIU of heparin/ml were added to aliquots. After a one-hour incubation, 0.1 ml of 5 M NaCl was added to 0.4 ml of each of these samples and the mixtures were incubated at 25° C. for 30 min.

0.3 ml of a 1M solution of trichloroacetic acid was then added in each case and the mixtures incubated in an ice bath for 5 min. After centrifuging for 2 min, the supernatants (0.5 ml in each case) were chromatographed through an NAP-5 column (from Pharmacia Biotech GmbH) and the eluates were collected.

The heparin was quantified as follows:
0.05 ml of sample or standard (heparin)
0.05 ml of AT III reagent (0.25 IU of AT III/ml, diluted in 100 mM tris/HCl, pH 7.5, 50 mM NaCl)
10 min incubation at 25° C.
0.05 ml of FXa reagent (Behring Diagnostics; OWLG)
3 min incubation at 25° C.
0.05 ml of FXa substrate (Behring Diagnostics; OWLH)
25 min incubation at 25° C.
0.05 ml of 50% acetic acid
Measurement of the $OD_{405nm}$ and evaluation using the heparin standard curve which has been included.

The heparin standard curve was constructed in a concentration range of from 0 to 200 mIU/ml (0/3.125/6.25/12.5/25/50/100/200 mIU of heparin/ml). The concentrations were plotted against the $\Delta OD$ and the heparin concentrations were calculated using this curve. These determinations were in each case carried out on three consecutive days.

Result

|  | Heparin (mIU/ml) Mean value ± Standard deviation |
|---|---|
| AT III control (not supplemented) | <10 |
| AT III + 20 mIU of heparin/ml | 24.4 ± 6.3 |
| AT III + 50 mIU of heparin/ml | 49.5 ± 5.3 |
| AT III + 80 mIU of heparin/ml | 82.9 ± 3.8 |

What is claimed is:

1. A process for determining the amount of a glycosaminoglycan in an antithrombin III (ATIII)-containing solution, which comprises:
   a) increasing the ionic strength of the AT III-containing solution until the glycosaminoglycan is released,
   b) removing the AT III which has been released from the glycosaminoglycan from the solution,
   c) desalting and determining the amount of glycosaminoglycan which has remained in the solution.

2. The process as claimed in claim 1, wherein the ionic strength in step a) is adjusted to between 15 mS and 250 mS.

3. The process as claimed in claim 1, wherein AT III is removed by acid precipitation.

4. The process as claimed in claim 1, wherein desalting is carried out by gel filtration.

5. The process as claimed in claim 1, wherein the glycosaminoglycan is heparin.

* * * * *